United States Patent [19]

Ham et al.

[11] Patent Number: 5,324,656
[45] Date of Patent: * Jun. 28, 1994

[54] MEDIA FOR NORMAL HUMAN MUSCLE SATELLITE CELLS

[75] Inventors: Richard G. Ham; Judith A. St. Clair, both of Boulder, Colo.; Zetan Nie, Boston, Mass.

[73] Assignee: University of Colorado Foundation, Inc., Boulder, Colo.

[*] Notice: The portion of the term of this patent subsequent to Sep. 1, 2009 has been disclaimed.

[21] Appl. No.: 928,958

[22] Filed: Aug. 12, 1992

Related U.S. Application Data

[62] Division of Ser. No. 265,785, Nov. 1, 1988, Pat. No. 5,143,842.

[51] Int. Cl.$^5$ .......... C12N 5/00; C12N 5/08; C12N 5/06
[52] U.S. Cl. .......... 435/240.2; 435/240.21; 435/240.3; 435/240.31
[58] Field of Search .......... 435/240.31, 240.3, 240.2, 435/240.21

[56] References Cited

U.S. PATENT DOCUMENTS 4,443,546 4/1984 Stemerman et al.

OTHER PUBLICATIONS

Hauschka (1974) Dev. Biol. 37:329–344.
Ham (1963) Exp. Cell Res. 29:515–526.
Blau et al. (Sep. 1981) Proc. Natl. Acad. Sci. USA, vol. 78, No. 9 pp. 5623–5627.
Blau et al. (1983) Proc. Natl. Acad. Sci. USA 80:4856–4860.
Askansas et al. (1985) Arch. Neurol. 42:749–752.
Allen et al. (1985) In Vitro Cell. Dev. Biol. 21:636–640.
Knedler et al. (1987) In Vitro Cell. Dev. Biol. 23(7):481–491.
Askansas et al. (1985) Soc. Neurosci. Abstr. 11:936.
Delaporte et al. (1986) Biol. Cell. 57:17–22.
Yasin et al. (1983) in Hormonally Defined Media: A Tool in Cell Biology Fisher and Weiser (eds.), Springer-Verlag, Berlin, pp. 406–410.
Law et al. (1990) Adv. Exp. Med. Biol. 280:241–250.
Karpati et al. (1990) Adv. Exp. Med. Biol. 208:31–34.
Webster et al. (1988) Exp. Cell Res. 174:252–265.
Law et al. (1988) Muscle and Nerve 11:525–533.
Florini et al. (1979) In Vitro 15:983–992.
Pederson et al. (1947) J. Phys. Colloid Chem. 51:164–171.
Ham et al. (1964) Biochem. Biophys. Res. Comm. 14:34–38.
McKeehan et al. (1978) Biochem Biophys. Res. Com. 80:1013–1021.
Nie et al. (1990) Biochem. Biophys. Res. com. 178:959–966.
Ham et al. (1988) In Vitro Cell. Dev. Biol. 24(8):833–844.
Fisher et al. (1958) Proc. Natl. Acad. Sci. USA 44:4–10.

(List continued on text page.)

Primary Examiner—George C. Elliott
Attorney, Agent, or Firm—Greenlee & Winner

[57] ABSTRACT

An improved basal nutrient medium MCDB 120 for the clonal growth of human muscle satellite cells (HMSC) is described. In addition, serum-free supplements for the clonal growth of HMSC containing serum albumin, dexamethasone, fetuin fraction mitogen, epidermal growth factor and insulin are described. Combination of MCDB 120 and the serum-free supplement results in a serum-free medium for growth of HMSC, which can be transplanted to muscles of patients afflicted with muscle degenerative diseases such as muscular dystrophy. The serum-free supplement can also be used with other basal nutrient media such as MCDB 131M for growth of HMSC. Addition of 5% dialyzed fetal bovine serum to the serum-free media described results in semi-defined media which allows significantly improved growth of HMSC.

15 Claims, 4 Drawing Sheets

OTHER PUBLICATIONS

Puck et al. (1968) Proc. Natl. Acad. Sci. USA 59:192–199.
Salomon et al. (1981) Proc. Natl. Acad. Sci. USA 78:382–386.
Spiro (1960) J. Biol. Chem. 235:2860–2869.
Fisher et al. (1962) Arch. Biochem. Biophys. 99:241–248.
Marr et al. (1962) Biochem. Biophys. Acta 63:276–285.
Feldman et al. (1984) J. Biol. Chem. 259:4458–4462.
Libby et al. (1985) J. Cell. Physiol. 125:357–366.
Florini (1987) Muscle & Nerve 10:577–598.
Green et al. (1963) J. Biol. Chem. 238:3640–3644.
Loskutoff (1978) J. Cell. Physiol. 96:361–370.
Ham et al. (1990) Adv. Exp. Med. Biol. 280:193–199.
Swenson et al. (1979) J. Biol. Chem. 254(11):4452–4456.
Huard et al. (1991) Clin. Sci. 81:287–288.
Huard et al. (1992) Muscle & Nerve 15:550–560.
Ham et al. (1979) Methods in Enzymology LVIII:8-9–93.
Ham et al. (1981) Hbk. Exp. Pharmacol. 57:13–88.

MEDIA FOR NORMAL HUMAN MUSCLE SATELLITE CELLS

RELATEDNESS OF THE APPLICATION

The subject application is a divisional of copending U.S. Ser. No. 265,785, filed Nov. 1, 1988 now U.S. Pat. No. 5,143,842.

BACKGROUND OF THE INVENTION

In the conduct of certain cell biology research, the growth and maintenance of cells derived from animal and human tissues is essential. For example, tissue culture is used extensively in studies of inherited disorders in both animals and humans. Tissue culture of human muscle cells is of particular interest for the study of human muscle cell disorders. While in vitro growth of human skeletal muscle cells has been achieved, relatively little attention has been given to the development of culture media optimized specifically for these cells.

The development of serum-free media for cell growth allows the identification of cell growth factors and allows detailed biochemical and metabolic studies of the cell. For example, the use of serum-free media for the growth of human muscle cells facilitates the investigation of the role of growth factors in muscle differentiation. Such studies are important in the determination of the biochemical basis of certain muscle disorders.

Clonal growth of mononucleate cells from embryonic chicken skeletal muscle and their fusion and differentiation to form multinucleate contractile myotubes was achieved relatively early in the history of modern cell culture ( see, for example, Konigsberg, I. R. (1963) Science 140:1273-1284). Growth of human skeletal muscle cells in vitro was also achieved quite early (Hauschka, S. D. (1974) Dev. Biol. 37:329-344). However, despite many years of studies on growth and differentiation of skeletal muscle cells in vitro, relatively little attention has been given to the development of culture media optimized specifically for growth of muscle cells from humans or other species.

Both undefined and defined media have been described for the growth of muscle cells in culture. Nutrient medium F10 (Ham, R. G. (1963) Exp. Cell Res. 29:515-526), originally developed for Chinese hamster ovary cells, was used with addition of serum and chicken embryo extract to grow chicken embryo muscle cells (Hauschka, S. D. (1966) Proc. Natl. Acad. Sci. USA 55:119-126) and later for growth of human muscle cells (Hauschka, S. D. (1974) supra). F10 plus serum and embryo extract has been widely used for muscle cell culture, in particular, for the establishment of clonal cultures from normal and diseased human muscle cells (Blau, H. M. and Webster, C. (1981) Proc. Natl. Acad. Sci. USA 78:5623-5627; Blau, H. M. and Webster, C. (1983) Proc. Natl. Acad. Sci. USA 80:4856-4860). The most frequently used alternative is Dulbecco's modified Eagle's medium (DME). Other nutrient media that have been used for muscle cell culture, sometimes in combination with DME, include M199 (Askanas, V. and Engel, W. K. (1975) Neurology 25:58-67; Konigsberg, I. R. (1963) supra), MEM plus nonessential amino acids, pyruvate and additional vitamins (Miranda, A. F. et al. (1979) in *Muscle regeneration*, Mauro, S. et al. (eds.), Raven Press, New York, pp 453-473), RPMI 1640 (Hayashi, I. and Kobylecki, J. (1982) Cold Spring Harbor Conf. on Cell Prolif. 9:857-865), F12 (Pinset, C. and Whalen, R. G. (1985) Dev. Biol. 108:284-289), F14 (Askanas, V. and Gallez-Hawkins, G. (1985a) Arch. Neurol. 42:749-752; Vogel, Z. et al. (1972) Proc. Natl. Acad. Sci. USA 69:3180-3184), MCDB 104 (Allen, R. E. et al. (1985) In Vitro Cell. Dev. Biol. 21:636-640), and MCDB 201 (Dollenmeier, P. etal. (1981) Exp. Cell Res. 135:47-61). Although a number of these media have become standard in their applications, they are suboptimal for efficient promotion of clonal growth of human muscle satellite cells (HMSC).

Often, the culturing of cell types requires the addition of supplements to a basal nutrient medium. These supplements are generally chemically undefined, for example in the form of serum and embryo extract. For many purposes, the use of an undefined supplement is satisfactory. However, for studying growth, metabolism, and/or differentiation of muscle cells in culture, it is desirable to have a supplement that is defined or semi-defined. The introduction of undefined components to the cell culture can contribute to variability in biochemical study results.

Direct replacement of serum with supplements of better defined composition has generally not been very successful for growth of normal cells in conventional basal nutrient media. The amount of undefined supplementation needed for good growth can be reduced or eliminated by optimizing a particular basal nutrient medium (Ham,R. G. (1984) in *Methods for Preparation of Media, Supplements, and Substrata for Serum-Free Animal cell culture,* Alan R. Liss, Inc. New York, pp. 3-21). For example, a basal nutrient medium, MCDB 131, optimized for growth of human microvascular endothelial cells supported clonal growth with as little as 0.7% dialyzed fetal bovine serum (dFBS) when also supplemented with epidermal growth factor (EGF) and hydrocortisone (Knedler, A. and Ham, R. G. (1987) In Vitro Cell. and Develop. Biol. 23(7):481-491).

Previous defined media for normal HMSC (Askanas, V. et al. (1985b) Soc. Neurosci. Abstr. 11:936; Delaporte, C. et al. (1986) Biol. Cell. 57:17-22; Yasin, R. and van Beers, G. (1983), in *Hormonally Defined Media: A Tool in Cell Biology,* Fischer, G. and Weiser, R. (eds.), Springer Verlag, Berlin, pp. 406-410) have utilized either DME or F14 (Vogel, Z. et al. (1972) supra) as the nutrient medium without further optimization. These defined media favor differentiation of HMSC rather than optimal growth. In addition, when these media were used, initial inoculation of dense populations of cells into a serum-containing medium, followed by medium change to the serum-free formulation was required.

Askanas et al. (1985b) supra described a defined medium for the growth of HMSC. Basal nutrient medium F14 was used without further optimization. EGF, insulin, and BSA were included as components of the supplements in the medium.

Delaporte et al. (1986) supra developed three defined media for the growth of HMSC. The basal nutrient medium DME was used without further optimization. Insulin was employed in the supplement used in these media. These media promote differentiation and inhibit myoblast proliferation.

Yasin and van Beers (1983) supra tested two defined media for the growth of HMSC. Again the basal nutrient medium DME was used without further optimization. In one medium, DME was supplemented with 0.5 mg/ml fetuin (Sigma type IV), $10^{-6}$ M insulin, and $10^{-7}$ M dexamethasone. In the other medium, DME was supplemented with 10-6 M insulin and 0.1 mg/ml L-thyroxine. However, it was found that serum was required for proliferation.

Stemerman et al. (U.S. Pat. No. 4,443,546, issued Apr. 17, 1984) entitled "Process and Composition for Propagating Mammalian Cells," purports to provide a serum-free media for normal mammalian cells. However, the specific media provided were developed for vascular smooth muscle cells and endothelial cells.

In addition to being useful for detailed biochemical and metabolic studies of HMSC, a serum-free medium is useful in producing HMSC relatively free of non-human antigens, which are suitable for transplantation into patients having muscle disorders such as muscular dystrophy. Myoblast transfer therapy has been undertaken in humans to treat Duchenne muscular dystrophy (Law, P. et al. (1990) Adv. Exp. Med. Biol. 280:241-250. In transplantation of HMSC to humans, it is preferred that MHC (major histocompatibility complex) or HLA (human leukocyte antigens) be matched to minimize the necessity of immunosuppressive drugs such as cyclosporin A and FK 506. However, as discussed by Karpati, G. (1990) Adv. Exp. Med. Biol. 208:31-34, immunorejection of cultured myoblasts or satellite cells due to MHC incompatibility may be low because human myoblasts express very little MHC I and essentially no MHC II. Minor histocompatibility factors may also be matched between donor and recipient, though these are difficult to detect in myoblasts.

In addition to minimizing immune rejection arising from major or minor histoincompatibility, immune rejection due to anaphylactic or antibody response to non-human antigens present in the transplanted cells should be avoided. A potential source of nonhuman antigens is the medium supplement which has, prior to the subject application, contained animal serum or extracts. Repeated injections of the cell preparation containing non-human antigens can sensitize the recipient, and perhaps ultimately result in an anaphylactic reaction. Karpati, G., supra, recommends using human serum in the culture medium to reduce this problem. However, since the human serum must be type matched to that of the recipient, the presence of a blood borne disease entity (e.g., HCV) must be considered. If the patient's own serum is used in the medium (typically at 10% (v/v) serum), consideration must be given to the stress on the patient.

Previously, Webster, C. et al. (1988) Exp. Cell Res. 174:252-265, have developed a fluorescence activated cell sorting (FACS) method for sorting of myoblasts from fetal muscle tissue. They have been able to recover $10^4$ myoblasts from 0.1 g of fetal tissue. The FACS preparations are reported to be 99% myoblasts. Law, P. et al. (1988) Muscle & Nerve 11:525-533, have used about $10^6$ myoblasts in murine muscle transplants. Therefore, the FACS prepared cells must be amplified by culturing if they are to be used for transplantation. During the culturing process, non-human antigens can be introduced by the use of serum-containing supplements in the culture medium.

Moreover, as discussed in Karpati, G., supra, to avoid the presence of other cells such as fibroblasts (which express MHC I), it may be preferable to use clonally grown myoblasts. These also must be amplified in culture to produce cell populations large enough for transplantation.

Thus, there is a clear need for a method of growing human myoblast populations that are relatively free of non-human antigens, and therefore useful in human transplantation. Such populations could be produced by growing myoblasts in serum-free medium.

SUMMARY OF THE INVENTION

The present invention provides a nutrient medium, designated MCDB 120 herein, optimized for the growth of human muscle satellite cells (HMSC). Table 1 provides the composition of MCDB 120. Clonal growth of HMSC was sensitive in particular to the concentrations of the medium components L-arginine, L-methionine, L-threonine, D-pathothenic acid and myo-inositol. It is believed that MCDB 120 is the first optimized basal nutrient medium that has been developed specifically for the in vitro culture of HMSC. Table 1 also provides MCDB 131M as a second medium used in the methods of the subject invention.

This invention also provides serum-free supplements for the growth of HMSC which contain: serum albumin, dexamethasone, epidermal growth factor (EGF), fetuin fraction mitogen and insulin. The serum-free supplements include SF, which contains about 0.5 mg/ml serum albumin; about $1 \times 10^{-6}$M dexamethasone; about $3 \times 10^{-5}$M insulin; about 10 ng/ml epidermal growth factor (EGF) and about 0.5 mg/ml Pedersen fetuin. Alternative serum free supplements can replace Pedersen fetuin with purer mitogen preparations. The serum-free supplements can optionally include between about 3–30 ng/ml fibroblast growth factor (FGF). The addition of the abovedescribed serum-free supplements to MCDB 120 or MCDB 131M basal nutrient medium provides serum-free media, which give improved clonal growth of HMSC. Serum-free supplemented MCDB 120 (MCDB 120+SF) provides better growth of HMSC than serum-free supplemented MCDB 131M and thus is preferred.

TABLE 1

| Composition of MCDB 120 and MCDB 131M | | |
|---|---|---|
| | MCDB 120 moles/liter | MCDB 131M[1] moles/liter |
| AMINO ACIDS | | |
| L-Alanine | $3 \times 10^{-5}$ | |
| L-Arginine.HCl | $1 \times 10^{-3}$ | $3 \times 10^{-4}$ |
| L-Asparagine.H$_2$O | $1 \times 10^{-4}$ | |
| L-Aspartic Acid | $1 \times 10^{-4}$ | |
| L-Cysteine.HCl.H$_2$O | $2 \times 10^{-4}$ | |
| L-Glutamic Acid | $3 \times 10^{-5}$ | |
| L-Glutamine | $1 \times 10^{-2}$ | |
| Glycine | $3 \times 10^{-5}$ | |
| L-Histidine.HCl.H$_2$O | $2 \times 10^{-4}$ | |
| L-Isoleucine | $5 \times 10^{-4}$ | |
| L-Leucine | $1 \times 10^{-3}$ | |
| L-Lysine.HCl | $1 \times 10^{-3}$ | |
| L-Methionine | $2 \times 10^{-4}$ | $1 \times 10^{-4}$ |
| L-Phenylalanine | $2 \times 10^{-4}$ | |
| L-Proline | $1 \times 10^{-4}$ | |
| L-Serine | $3 \times 10^{-4}$ | |
| L-Threonine | $3 \times 10^{-4}$ | $1 \times 10^{-4}$ |
| L-Tryptophan | $2 \times 10^{-5}$ | |
| L-Tyrosine | $1 \times 10^{-4}$ | |
| L-Valine | $1 \times 10^{-3}$ | |
| VITAMINS | | |
| d-Biotin | $3 \times 10^{-8}$ | |
| Folinic Acid (Ca salt).5H$_2$O | $1 \times 10^{-6}$ | |
| DL-alpha-Lipoic Acid | $1 \times 10^{-8}$ | |
| Niacinamide | $5 \times 10^{-5}$ | |
| D-Pantothenic Acid (Hemi-Ca salt) | $1 \times 10^{-4}$ | $5 \times 10^{-5}$ |
| Pyridoxine.HCl | $1 \times 10^{-5}$ | |
| Riboflavin | $1 \times 10^{-8}$ | |
| Thiamin.HCl | $1 \times 10^{-5}$ | |
| Vitamin B12 | $1 \times 10^{-8}$ | |
| OTHER ORGANIC | | |

TABLE 1-continued

Composition of MCDB 120 and MCDB 131M

| | MCDB 120 moles/liter | MCDB 131M[1] moles/liter |
|---|---|---|
| COMPONENTS | | |
| Adenine | $1 \times 10^{-6}$ | |
| Choline Chloride | $1 \times 10^{-4}$ | |
| D-Glucose | $5.56 \times 10^{-3}$ | |
| myo-Inositol | $1 \times 10^{-4}$ | $4 \times 10^{-5}$ |
| Putrescine.2HCl | $1 \times 10^{-9}$ | |
| Sodium Pyruvate | $1 \times 10^{-3}$ | |
| Thymidine | $1 \times 10^{-7}$ | |
| BULK INORGANIC SALTS | | |
| $CaCl_2.2H_2O$ | $1.6 \times 10^{-3}$ | |
| KCl | $4 \times 10^{-3}$ | |
| $MgSO_4.7H_2O$ | $1 \times 10^{-3}$ | |
| NaCl | $1.1 \times 10^{-1}$ | |
| $Na_2HPO_4.7H_2O$ | $5 \times 10^{-4}$ | |
| TRACE ELEMENTS | | |
| $CuSO_4.5H_2O$ | $1 \times 10^{-8}$ | $5 \times 10^{-9}$ |
| $FeSO_4.7H_2O$ | $3 \times 10^{-6}$ | $1 \times 10^{-6}$ |
| $H_2SeO_3$ | $3 \times 10^{-8}$ | |
| $MnSO_4.5H_2O$ | $1 \times 10^{-9}$ | |
| $Na_2SiO_3.9H_2O$ | $1 \times 10^{-5}$ | |
| $(NH_4)_6Mo_7O_{24}.4H_2O$ | $3 \times 10^{-9}$ | |
| $NH_4VO_3$ | $5 \times 10^{-9}$ | |
| $NiCl_2.6H_2O$ | $3 \times 10^{-10}$ | |
| $ZnSO_4.7H_2O$ | $3 \times 10^{-7}$ | $1 \times 10^{-9}$ |
| BUFFERS, INDICATORS AND MISCELLANEOUS | | |
| Phenol Red (Na salt)[2] | $3 \times 10^{-6}$ | $3 \times 10^{-5}$ |
| $NaHCO_3$[3] | $1.4 \times 10^{-2}$ | |

[1]Concentrations in MCDB 131M are listed only when they differ from those in MCDB 120. MCDB 131M is MCDB 131 (Knedler and Ham, 1987) with magnesium sulfate reduced to 1.0 mM.
[2]Phenol red is a pH indicator whose concentration, as long as it is kept below toxic levels, is not critical to growth.
[3]To insure a correct final pH with 5% carbon dioxide incubation, the pH of the medium should be adjusted to pH 7.4 in air at room temperature prior to addition of the sodium bicarbonate. The final osmolarity of the completed medium (with bicarbonate) should be 270 +/− 5 mOsm/kg.

In contrast, addition of SF to conventional media such as F10 does not result in media adequate for growth of HMSC. Good clonal growth of HMSC can be achieved from direct inoculation of these serum-free media with a small number of trypsinized cells. In addition these serum-free media strongly favor growth of HMSC with relatively little fusion and myotube differentiation. HMSC grown in the serum-free media of this invention still retain the capacity to fuse and differentiate when transferred to an appropriate medium that promotes differentiation. Prior to this invention, reasonable serum-free clonal growth of HMSC had not been achieved. This work is believed to represent the first time that a dual approach involving both systematic optimization of the nutrient medium and replacement of undefined supplements with hormones, growth factors, and other more defined substances has been applied to growth of human skeletal muscle cells or to skeletal muscle cells from any species. The media of the present invention can also be employed for the growth of muscle cells of other species and for the growth of other human cells types.

In addition, this invention provides semi-defined media for the growth of HMSC. Semi-defined HMSC medium is prepared by the addition of at least about 5.0% (v/v) dialyzed fetal bovine serum (dFBS) to serum-free supplemented MCDB 120 or serum-free supplemented MCDB 131M. Media supplemented with dFBS are designated doubly supplemented. The addition of dFBS to the serumfree supplemented media results in clonal growth of HMSC that far exceeds that in previously described media with any amount of serum, and results in monolayer growth that is at least equal to that in conventional media, such as F10 or DME, with higher levels of serum.

In another aspect, the present invention provides an improved method for the clonal growth of HMSC which employs the serum-free supplemented media and semi-defined media described herein.

In another aspect, the present invention provides an improved method for the culturing of HMSC to produce progeny that are relatively free of non-human antigens, and are therefore more suitable for transplantation to human recipients than media containing non-human antigens. The HMSC are grown on MCDB 120 or 131M medium and a serum free supplement. Serum free supplements comprising dexamethasone, serum albumin, epidermal growth factor, and Pedersen fetuin or fetuin replacing mitogen preparations (as discussed herein) can be used with MCDB 120 or 131M to produce myoblasts relatively free from non-human antigens.

DETAILED DESCRIPTION OF THE INVENTION

Figure 1:
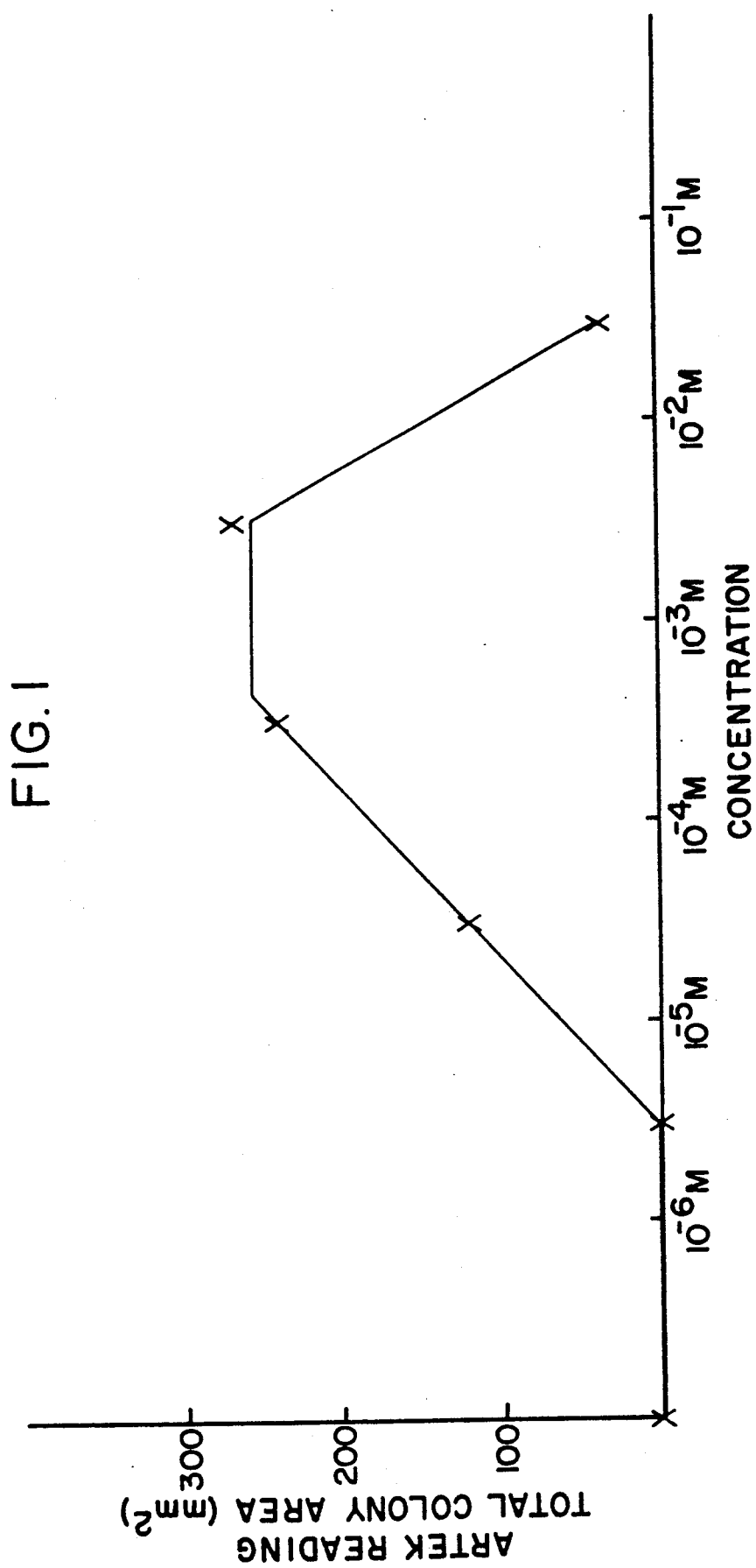
FIG. 1 is a graph showing the growth response curve of HMSC for variation of the concentration of arginine in MCDB 131M+5% dFBS and 0.5% dBPE. Cell growth is assessed as described in Example 3 as total colony area (mm²)/dish. The concentration of arginine was measured in molar (moles/liter) units. Concentration is plotted on a logarithmic scale. As shown in Table 1, the optimal concentration of arginine chosen for use in the optimal concentration of arginine chosen for use in MCDB 120 was $1 \times 10^{-3}$ M.

The following definitions are provided to clarify their meaning in the specification and the claims.

Human muscle satellite cells are the mononucleated myoblasts of mature muscle fiber, and are responsible for postnatal muscle growth and regeneration in vivo.

Human muscle satellite cell progeny are daughter cells produced by culturing human muscle satellite cells in a culture comprising a medium, such as MCDB 120 or 131M, and a supplement. Progeny cells when used for transplantation are present in numbers of at least about $10^6$ cells. Increasingly preferred are progeny populations of at least about $10^7$, $10^8$, $10^9$ and $10^{10}$.

A basal nutrient medium is one that satisfies all cellular requirements for nutrients. A nutrient, from a cell culture perspective, is defined as a chemical substance that enters a cell and is used as a structural component, as a substrate for biosynthesis or energy metabolism or as a catalyst (cofactor) in such processes. For example, trace elements and vitamins are nutrients (Ham, R. G. 1984 supra). Anything else needed for cellular proliferation is normally classified as a supplement, including all undefined additives such as serum and pituitary extract. Supplements satisfy non-structural cellular growth requirements and make possible growth of the cells in the basal nutrient medium.

In a defined medium the chemical composition of all components are known. In an undefined medium, the chemical compositions of certain components are unknown, for example, serum and embryo or pituitary extract (herein called "undefined supplement") contain a number of high and low molecular weight components only some of which may be required for the growth of culturing cells. For studying the growth, metabolism, and/or differentiation of muscle cells in culture, it is desirable to have a medium that is defined. Although a completely defined medium which allows optimal cell growth is most desirable, it can be difficult to achieve. Media preparation often requires the inclusion of defined and undefined components to achieve adequate cell growth. Significant enhancement of cell growth may be achieved by the inclusion of small quantities of one or more undefined components. As used herein, the term semi-defined medium refers to a medium, capable of supporting cell growth, that has a minimum of undefined components.

OPTIMIZED NUTRIENT MEDIUM

Although nutrient medium F10 supported reasonably good growth of HMSC with 5% dFBS and 0.5% dBPE, a number of alternative media were tested, including MEM, DME, F12, DME:F12 (1:1), m199, McCoy's 5a, RPMI 1640, MB752/1, MCDB 110, MCDB 131, MCDB 153, MCDB 170, and MCDB 202, some of which had previously been employed for growth of muscle cells, and several from the MCDB series that had been optimized for clonal growth of other types of normal cells (Ham, R. G. (1984) in Cell Separation: Methods and Selected Applications, Vol. 3, Orlando, Fla., Pretlow, T. G. and Pretlow, T. P. (eds.) Academic Press, pp. 209-236) to determine how well they would support growth of HMSC with these supplements. Among the media tested, MCDB 131 (Knedler, A. and Ham, R. G. supra) was found to be the best for clonal growth of HMSC. MCDB 131 had other desirable attributes, such as a complete set of added trace elements.

The clonal growth response of HMSC to varying amounts of magnesium indicated that the concentration in MCDB 131 should be reduced. A modification of MCDB 131 with its magnesium ion concentration reduced to 1.0mM (MCDB 131M) was therefore selected as the nutrient medium used in detailed studies of qualitative and quantitative nutrient requirements for growth of HMSC. Most of the nutrient growth-response titrations leading to MCDB 120 were done with 5.0% dFBS and 0.5% dBPE supplementation.

Nutrient medium MCDB 120 was developed by omitting the media components of MCDB 131M one at a time and adding them back over a wide range of concentrations to determine the optimal amount of each for clonal growth of HMSC with 5% dFBS and 0.5% dBPE. For a given required component of the nutrient medium, there will, in general, be a plateau region in the growth response curve, where the substance has ceased to be the rate limiting factor for cellular multiplication due to deficiency, and where its concentration has not yet reached a level that is rate-limiting for cellular multiplication because of inhibitory or toxic effects (Ham, R. G. (1984) Supra). The concentration plateau can be broad or narrow depending of the component tested, with the concentration of certain components being more critical to growth than other components. One of the objectives of optimization is to adjust all components of the basal nutrient medium to concentrations that are near the midpoints of their plateaus on a semi-logarithmic plot of optimum growth. The use of a logarithmic scale for concentrations is important. The concentration midpoint on such a plot is equidistant from the ends of the concentration plateau. Linear plots of concentration distort toward high concentrations. In FIG. 1, the HMSC growth response curve as a function of the variation of the concentration of arginine is shown. As noted in Table 1, the optimal concentration of arginine chosen for MCDB 120 was $1 \times 10^{-3}$M.

Optimization of MCDB 131M for growth of HMSC indicated that arginine, methionine, threonine, pantothenate, and inositol should be increased. In addition, although there were not well defined requirements for iron, zinc, or copper in media containing both dFBS and dBPE, their levels in MCDB 131M were low enough to be potentially rate-limiting with defined supplements. Therefore, they were increased to levels known to be effective for other cell types, and shown by titrations not to be inhibitory for HMSC.

Subsequent testing in the serum-free medium described below has demonstrated clearly that iron was required. The higher levels of copper and zinc in MCDB 120 also appeared to be marginally beneficial for serum-free growth, although a major requirement could not be demonstrated, probably due to high background levels of these metal ions in other medium components.

Individual growth-response titrations in MCDB 131M also suggested that reductions in the concentrations of cysteine, glutamine, tyrosine, lipoic acid, and phenol red might be beneficial. However, when all of these reductions (except phenol red) were combined in a single medium, growth was reduced, both in MCDB 131M and in MCDB 120, possibly due to alternative requirements for higher levels of one or the other of the components. The effect on growth was relatively small and appeared to involve complex balance relationships, so it was elected to retain the concentrations of these components, except phenol red, as in MCDB 131M. The concentration of phenol red was reduced to $3.3 \times 10^{-6}$ M. Phenol red is employed in the medium as a pH indicator and is not critical to the function of the medium.

Figure 2:
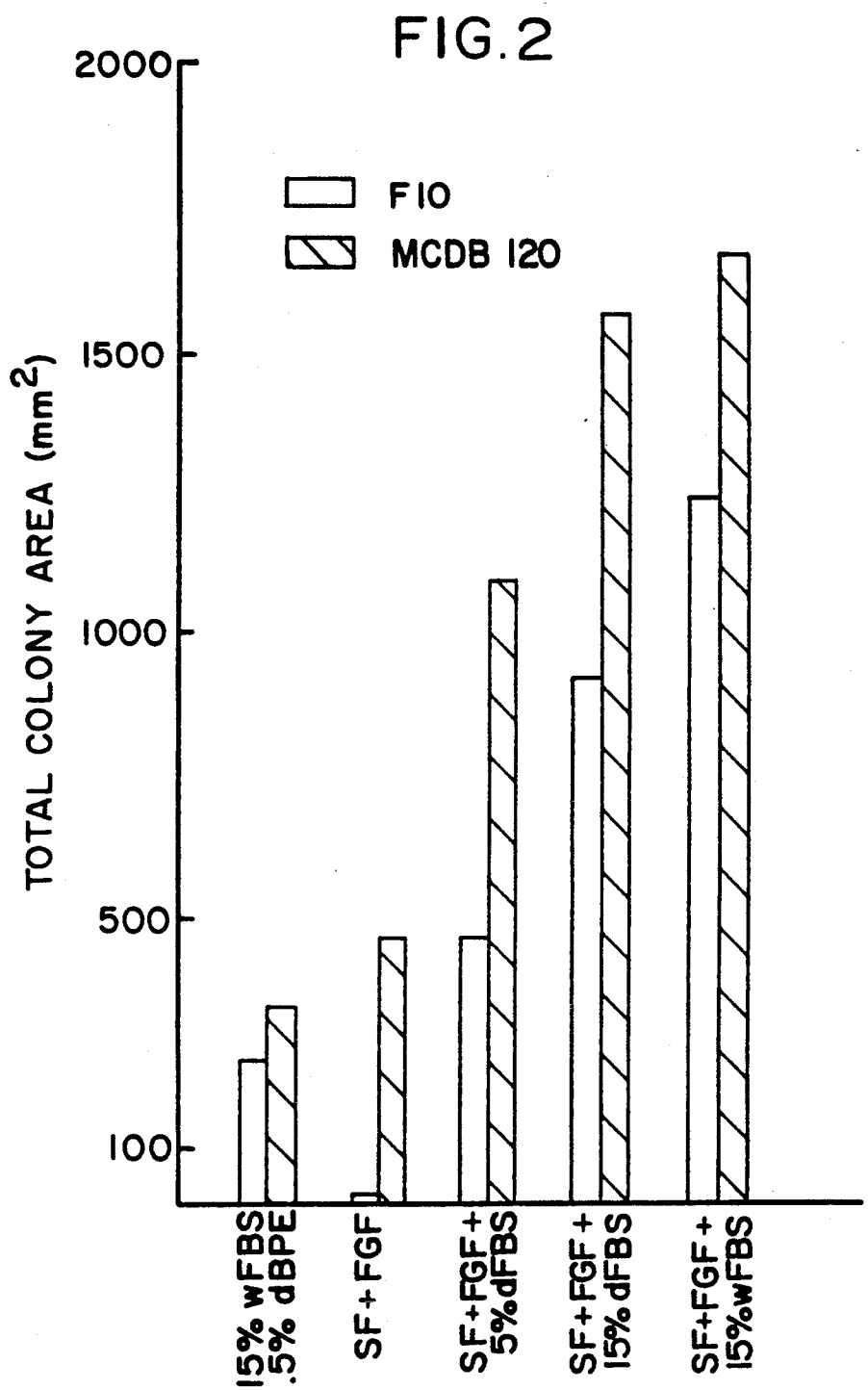
FIG. 2 is a graph showing clonal growth of HMSC in medium MCDB 120 with various supplements. Each 60mm petri dish received an inoculum of 200HMSC added to 5.0 ml of MCDB 120 supplemented as indicated. After 14 days without medium change, the colonies were fixed, stained and colony area/dish was determined as described in Example 3.

In summary, MCDB 120 differs from MCDB 131M in its levels of arginine, methionine, threonine, pantothenate, inositol, iron, zinc, and copper, all of which have been increased, and in its level of phenol red, which has been reduced. Medium MCDB 120 supports better clonal growth of HMSC than MCDB 131M, both with serum-free supplementation and with low levels of serum and embryo extract. FIG. 2 illustrates that MCDB 120 is an increasingly superior medium to F10 when used with lower levels of serum supplementation. Whether used with a serum free or an undefined supplement, MCDB 120 is a superior medium for clonal growth of HMSC as compared to F10, DME, M199, MEM, RPMI1640, MCDB 104, F14, or MCDB 201.

SERUM-FREE SUPPLEMENTS

The starting point for the determination of serum-free supplements was growth medium GM-1 (Blau, H. M. and Webster, C. (1981) supra), which contained 15% fetal bovine serum and 0.5% chicken embryo extract in nutrient medium F10 (Ham, R. G. (1963) supra). It was found that bovine pituitary extract (BPE), which is an effective supplement for a variety of other cell types (Boyce, S. T. and Ham, R. G. (1983) J. Invest. Dermatol. 81(1), Suppl.:33s-s; Ham, R. G. et al. (1987), in *Growth and differentiation of mammary epithelial cells in culture*, Enami, J. and Ham, R. G. (eds.), Japan Scientific Societies Press, Tokyo, pp. 59-108; Hammond, S. L. et al. (1984) Proc. Natl. Acad. Sci. USA 81:5435-5439; Tsao, M. C. etal . (1982) J. Cell. Physiol. 110:219-229), at a concentration of 0.5% (70 µg/ml protein) supported growth equivalent to that obtained with 0.5% embryo extract, and that dialyzed BPE (dBPE) was equally effective. It was also found that 5% dFBS plus 0.5% dBPE supported an adequate level of clonal growth for nutrient growth-response studies, which are most effective when done with rate-limiting levels of dialyzed supplements (Ham, R. G. (1981) Hbk. Exp. Pharmacol. 57:13-88).

Pituitary extract is a known source of fibroblast growth factor (FGF), and FGF is known to stimulate growth of mononucleate muscle cells from various mammals and to inhibit their differentiation (Gospodarowicz, D. and Cheng, J. (1987) In Vitro Cell. Dev. Biol. 23:507-514; Gospodarowicz, D. et al. (1976) J. Cell Biol. 70:395-405; Lira, R. W. and Hauschka, S. D. (1982) Cold Spring Harbor Conf. on Cell Prolif. 9:877-884; Lim, R. W. and Hauschka, S. D. (1984a) J. Cell Biol. 98:739-747; Lira, R. W. and Hauschka, S. D. (1984b) Der. Biol. 105:45-58; Linkhart, T. A. et al. (1982) Cold Spring Harbor Conf. on Cell Prolif. 9:867-876). Commercial preparations of basic FGF (30 ng/ml) were found to fully replace the requirement of HMSC for dBPE in a background medium MCDB 131M or MCDB 120 plus 5% dFBS.

In preliminary tests, high purity full-length acidic FGF (prostatropin, Crabb, J. W. etal. (1986) Biochemistry 25:4988-4993) supported optimal growth of HMSC at 3 ng/ml. Basic FGF of comparable purity has not yet been tested, but literature reports suggest that it will be active at even lower concentrations (Gospodarowicz, D. et al. (1987) supra; Neufeld, G. and Gospodarowicz, D. (1986) J. Biol. Chem. 261:5631-5637).

Askanas and Gallez-Hawkins (1985a) supra, have reported that addition of a combination of FGF, EGF, and insulin to the culture medium for HMSC eliminates the requirement for embryo extract and reduces the amount of serum needed for growth, differentiation, and partial maturation. Although they did not specifically identify which component replaced the need for embryo extract, their results are consistent with the results described herein, both with regard to FGF, and with regard to EGF, which is discussed below.

In the presence of commercial basic FGF, dFBS was replaced with a mixture of defined and semi-defined supplements: bovine insulin, mouse EGF dexamethasone, bovine serum albumin and bovine fetuin. Preferred concentrations of these components were: bovine insulin, $3 \times 10^{-5}$M (180 µg/ml); mouse EGF, 10 ng/ml; dexamethasone, $1 \times 10^{-6}$M (0.4 µg/ml); bovine serum albumin (BSA), 0.5 mg/ml, and bovine fetuin (Pedersen), 0.5 mg/ml. The mixture of the five serum-replacing components are designated SF herein. The specific amounts of serum-free components are median concentrations for optimal growth of HMSC. It will be apparent to those in the art that the concentration of the individual components of the serumfree supplement can be varied; they can be increased until a toxic growth inhibitory effect is observed or decreased until cell growth is significantly inhibited. When MCDB 131M is supplemented with SF plus FGF, the resulting serum-free growth is at least as good as that obtained with 5% dFBS and 0.5% dBPE. HMSC growth in MCDB 120 supplemented with SF and FGF is equivalent to that in MCDB 120 supplemented with 5% dFBS and 0.5% dBPE.

Figure 3:
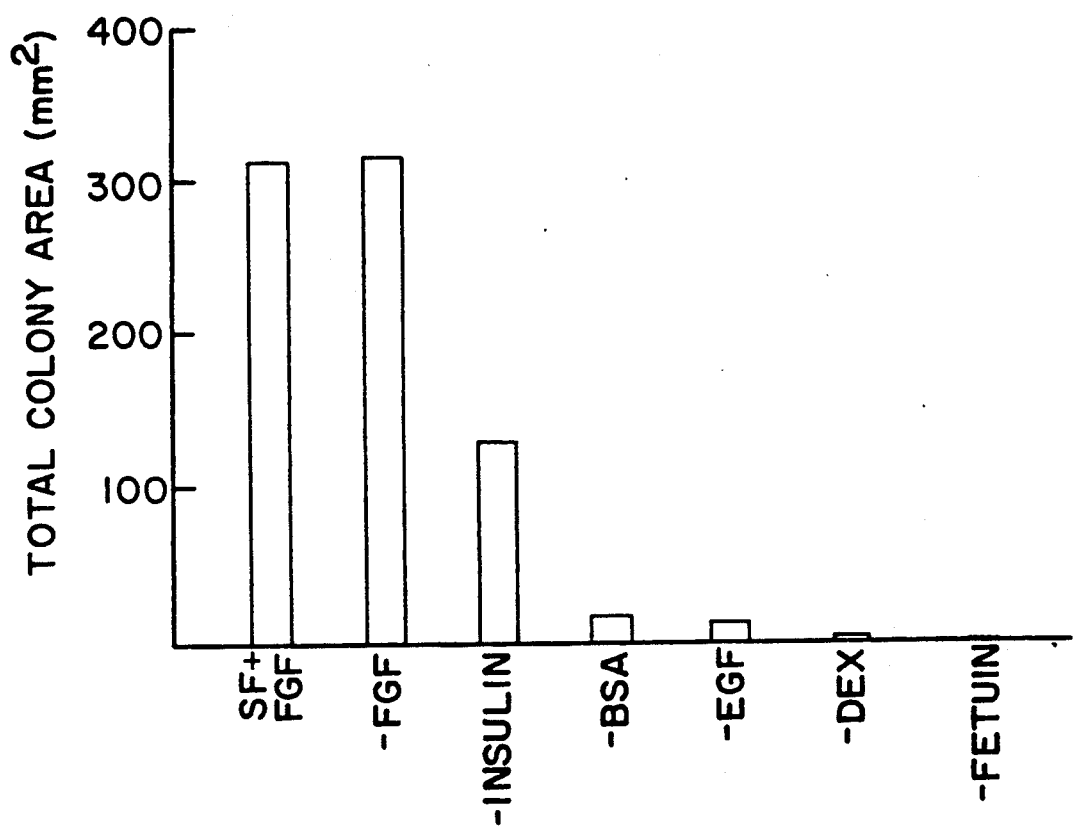
FIG. 3 is a graph of the effect of deletion of the individual components of SF on clonal growth of HMSC. The effect of addition of FGF on growth is also shown. Clonal cultures of HMSC were inoculated into MCDB 131M supplemented with complete SF plus 30 ng/ml FGF, or with the same mixture having the indicated components omitted. Total colony area/dish was determined after 14 days of growth, as described in Example 3.

Removal of any one of the five components of SF from a mixture of SF plus FGF reduces growth. The relative effects of the removal of the various components of SF on HMSC growth is shown in FIG. 3. There is sometimes also a reduction in growth of HMSC when FGF is removed, but the requirement for FGF in medium containing SF is far less stringent than when dFBS is the only other supplement employed. FGF could be omitted from media containing SF without significant decrease in HMSC growth. Because of the high cost of FGF and the minimal benefit from its presence, FGF was not included in the final formulation of serum-free growth supplement SF, and many of the experiments described below have been done without FGF. These data stand in sharp contrast to the major role that FGF appears to play in promoting growth and suppressing differentiation in myogenic mouse cell lines (Lim, R. W. and Hauschka, S. D. (1982) supra; Lim, R. W. and Hauschka, S. D. (1984a) supra; Lim, R. W. and Hauschka (1984b) supra; Linkhart, T. A. et al. (1981) Dev. Biol. 86:19-30)

Initial results showed that FGF failed to replace EGF in the serum-free supplement, SF. It has been determined that FGF is unstable in serum-free medium. In contrast, FGF appears to be stable in media containing serum. When stabilized with 1.0 µg/ml heparin, commercial basic FGF (at about 30 ng/ml) supports substantial serum-free growth of HMSC in the absence of EGF. However, growth in media containing EGF or EGF and stabilized FGF is usually better.

The five components of SF have all been employed in other serum-free or reduced serum media for muscle cells or muscle cell lines from various species (Allen, R. E. et al. (1985) supra; Askarias, V. et al. (1985b) supra; Delaporte, C. et al. (1986) supra; Dollenmeier, P. et al. (1981) supra; Florini, J. R. and Roberts,S. B. (1979) In Vitro 15:983-992; Gospodarowicz, D. and Cheng, J. (1987) supra; Kumegawa, M. et al. (1980) Der. Biol. 79:493-499; Yasin, R. and van Beers, G. (1983) Supra). In particular, insulin, dexamethasone and fetuin were included in medium MM-1 by Florini and Roberts (1979) supra and have been frequent components of more recent formulations. However, it is believed that no medium has been developed for HMSC that uses all five components.

Dexamethasone is presumed to act by stimulating glucocorticoid receptors. Hydrocortisone would be expected to replace dexamethasone. Contrary to expectations, growth equivalent to that observed with dexamethasone has not been obtained with hydrocortisone.

Fetuin (Sigma Type III) used in the SF is prepared commercially by the procedure of Pedersen, K. O. (1947) J. Phys. Colloid Chem. 51:164-171). The Pedersen fetuin fraction has had most of the bovine serum albumin removed. This preparation is a relatively crude ammonium sulfate fraction of fetal bovine serum protein, and cannot be considered to be fully "defined" in the strictest sense of the term. Hence, media containing it are generally referred to as "semi-defined" or "serum-free." In preliminary testing, fetuin prepared commercially (GIBCO) by the more rigorous procedure of Spiro, R. G. ( 1960 ) J. Biol. Chem. 235:2860-2869, was not active in test system employed. However, testing has not been performed on Spiro-type fetuin that has been subjected to exhaustive dialysis against chelating agents, which has been reported (Florini, J. R. and Roberts, S. B. (1979) supra) to remove inhibitory heavy metal residues that are introduced during the purification process. Preliminary data suggest that Pedersen-type fetuin may have at least three separate activities, including neutralization of residual trypsin and supplying polyamines (Ham, R. G. ( 1964 ) Biochem. Biophys. Res. Commun. 14:34-38).

As described in the Examples, it has been determined that other component(s) in the Pedersen fetuin, rather than fetuin itself, have the mitogenic activity. The mitogen has not yet been purified to homogeneity. However, fraction 50 PEG 2X prepared by the method of McKeehah, W. L. et al. (1978) Biochem. Biophys. Res. Com. 80:1013-1021, and combined fractions F14+15+16 of Nie, Z. et al. (1991) Biochem. Biophys. Res. Com. 178:959-966, have both demonstrated enhanced mitogen activity relative to Pedersen fetuin. Nie, Z. et al. use an additional column extraction not employed by McKeehan, W. L. et al. and produce a mitogen preparation of the greatest activity. Any of the Pedersen, McKeehan or Nie preparations can be used in the subject HMSC culture methods.

As used herein, "SF" refers to the serum free supplement comprising dexamethasone, serum albumin, epidermal growth factor, insulin, and Pedersen fetuin. "SF-i" refers to the serum free supplement comprising dexamethasone, serum albumin, epidermal growth factor, insulin and the McKeehan mitogen preparation. "SF-2" refers to the serum free supplement comprising dexamethasone, serum albumin, epidermal growth factor, insulin and the Nie mitogen preparation. HMSC progeny grown on MCDB 120 or 131M plus a supplement comprising dexamethasone, serum albumin, epidermal growth factor and the Pedersen fetuin are referred to as "materially pure" HMSC. HMSC progeny grown on MCDB 120 or 131M plus a supplement comprising dexamethasone, serum albumin, epidermal growth factor and the McKeehan mitogen preparation are referred to as "substantially pure" progeny. HMSC progeny grown on MCDB 120 or 131M plus a supplement comprising dexamethasone, serum albumin, epidermal growth factor and the Nie mitogen preparation are referred to as "essentially pure" progeny. Additionally, "essentially pure" cultured HMSC progeny refers to progeny cultured using supplements comprising dexamethasone, serum albumin, epidermal growth factor, and mitogen preparations representing further purifications of the Nie et al. mitogen preparation.

In the defined medium for rat muscle satellite cells developed by Allen et al. (1985) supra, bovine serum albumin (BSA) is described as a carrier for linoleic acid. However, in the present work, BSA was found to be highly stimulatory to clonal growth of HMSC without added linoleic acid and commercially delipidated BSA preparations were equally active. A detailed study of lipid metabolism or lipid requirements of HMSC has not been done. However, the serum-free medium described herein containing delipidated BSA supports extensive clonal growth of HMSC with no obvious source of preformed fatty acids, other than possible contaminants in fetuin or medium components.

BSA preparations that are certified for use in insulin RIA assays and crystalline BSA preparations that are described as "essentially globulin-free and essentially fatty acid free" had almost the same activity as ordinary BSA in the HMSC growth media. This suggests that the albumin itself is required. However, BSA is known to bind tightly to many different ligands, and supposed requirements for serum albumin have in the past usually proven to be requirements for other substances carried in the serum albumin.

In recent experiments, it has been observed that commercial preparations of human, pig, and horse serum albumin often support substantially better serum-free growth than similar preparations of bovine serum albumin.

Insulin is thought to stimulate rat muscle cell growth largely by cross reaction with receptors for the insulin-like growth factors (Dodson, M. V. and Allen, R. E. (1987) Tech. Ageing Dev. 39:121-138; Dodson, M. V. et al. (1985) Endocrinology 117:2357-2363; Ewton, D. Z. etal. (1987) Endocrinology 120:115-123; Florini, J. R. et al. (1984) In Vitro 20:942-958). Because of this, the levels of insulin needed in culture media for muscle cells are frequently at non-physiological high levels. The amount of insulin that we have found to be optimal for serum-free growth of HMSC is unusually high, even in comparison to other muscle cell media. This result suggests a requirement for a component that is an impurity in the insulin preparation. In addition, substantial growth sometimes occurs in the absence of added insulin. This result may be explained by the presence of impurities in other medium components, for example, BSA preparation may contain insulin growth factor I. However, to obtain consistent cell growth insulin has been included in the SF supplement.

EGF is mitogenic to a wide range of cell types, but has generally not been found to be stimulatory to non-human muscle cells. Dollenmeier et al. reported that EGF promoted growth of contaminating fibroblasts, but had little effect on embryonic chicken myoblasts. Allen et al. (1985) supra, found that EGF did not promote growth or differentiation of rat satellite cell cultures. Lim and Hauschka (Lim, R. W. and Hauschka, S. D. (1982) supra; Lim, R. W. and Hauschka, S. D. (1984b) supra) found that EGF is not mitogenic to mouse MM14 cell line, although these cells possess EGF receptors during the growth phase and lose them during commitment to the terminal differentiation, which is triggered by withdrawal of FGF. However, there is a differentiation 74-deficient variant of MM-14 designated DD-1, which does not require FGF for growth with 15% serum. Under low serum conditions, growth of DD-1 cells can be stimulated either with EGF or with FGF (Lim, R. W. and Hauschka, S. D. (1982) supra; Lim, R. W. and Hauschka, S. D. (1984b) supra). Differentiation-deficient mouse muscle line BC3H1 also exhibits a limited mitogenic response to EGF (Gospodarowicz, D. and Cheng, J. (1987) supra).

The effects of EGF on human muscle cells may be different than for muscle cells from other species that have been studied. Askanas and co-workers (Askanas, V. and Gallez-Hawkins (1985a) supra; Askanas, V. et al. (1985c) Neurosci. Lett. 61:213-219) have shown that EGF acts synergistically with FGF and insulin to promote growth, differentiation, and some aspects of maturation of cultured normal human muscle cells. EGF has been included in a serum-free medium for human muscle cells described in an abstract by Askanas et al. (1985b), but not yet published in detail. Lim and Hauschka (1982) supra, also mention the EGF binding capacity of early passage human myoblasts, but do not elaborate on its possible role. These reports, together with the data herein showing that EGF is needed for clonal growth of HMSC in our serum-free medium, suggest that there could be a species-based difference between HMSC and myoblasts or satellite cells from other vertebrate species with regard to the requirement for EGF. Species differences in receptor specificity are probably not involved, since mouse EGF is fully active for human muscle cells but does not stimulate the mouse MM-1 cell line. However, before firm conclusions are drawn, cells from other species need to be tested under conditions comparable to those we are using for HMSC.

As is appreciated by skilled artisans, when culturing cells to amplify for transplantation, it is preferable to reduce the nonhuman antigens that can be present in the serum supplement so as to reduce the potential for immunorejection by the recipient. When passaging/culturing HMSC in serum free supplements for purposes of transplantation, it is preferable to use human serum albumin instead of bovine serum albumin. Human serum albumin is commercially available (see Table 4 of Ham, R. et al. (1988) In Vitro Cell Devel. Biol. 24(8):833-844). Additionally, it is preferred to use EGF relatively free of non-human antigens, e.g., recombinant human EGF, instead of bovine EGF. Further, it is increasingly preferred to use the Pedersen fetuin preparation, McKeehan mitogen preparation and Nie mitogen preparation in the supplement.

The immunogenicity of HMSC progeny can be determined by methods known in the art. For example, as with antitoxins employing horse serum, patients who have received earlier HMSC progeny transplants can be tested for humoral and cell mediated immunorejection using skin tests, i.e., injecting HMSC cell preparations intradermally. Alternatively, an in vitro assay, such as an enzyme-linked immunosorbent assay, can be used. In such an assay, the patient's serum is assayed for antisera (IgG and optionally IgE) to the HMSC progeny preparation. In this way, immunogenicity of media or HMSC progeny preparations can be quantitated and compared.

The semi-defined serum-free medium for normal HMSC of the present invention was developed using a dual approach involving both the systematic optimization of the nutrient medium (Ham, R. G. (1981) supra) and the replacement of undefined supplements with hormones, growth factors, and other more defined substances (Barnes, D. and Sato, G. (1980) Anal. Blochem. 102:225-270). It is believed that this is the first time that such an approach has been applied to growth of skeletal muscle cells from any species. Previous defined media for normal HMSC (Askanas, V. et al. (1985b); Delaporte, C. et al. (1986) supra; Yasin, R. and van Beers, G. (1983) supra) have utilized either DME or F14 (Vogel, Z. (1972) supra) as the nutrient medium without further optimization. These defined media have also favored differentiation of HMSC rather than optimal growth. In contrast, serum-free media of the present invention strongly favor growth, with relatively little fusion and myotube differentiation. However, as will be described below, cells grown in these serum-free media retain the capacity to fuse and differentiate when transferred to an appropriate differentiation-promoting medium.

Another major advantage of the current serum-free medium is that one can routinely inoculate freshly trypsinized HMSC at clonal density directly into it. In previously described studies, the cells have generally been seeded into serum-containing media and then transferred to serum-free conditions after the cells have attached and become stabilized.

Clonal growth of HMSC in MCDB 120 or MCDB 131M supplemented with SF is consistently as good as with 5% dFBS plus 0.5% dBPE in the same nutrient medium. However, when 5% dFBS is added along with SF with or without FGF, clonal growth of normal HMSC in the resulting doubly supplemented media, designated DS herein, is greatly enhanced (about 130%). Colony forming efficiency is approximately 30% and the colonies that are formed are uniformly large and healthy appearing. Clonal growth in MCDB 120 DS (or MCDB 131M DS) substantially exceeds that previously obtained in conventional media such as F10 with pituitary (or embryo) extract and much higher levels of serum, and a modest further improvement (about 25%) can be obtained by increasing the level of serum (dFBS) in the DS medium to 15% (FIG. 2). Growth of monolayer cultures is also excellent in DS media.

It has been possible to establish primary clonal cultures directly in MCDB 131M DS or MCDB 120 DS without the need for conditioning of the medium or collagen coating of the wells, which were important features of the procedure used previously (Blau, H. M. and Webster, C. (1981) supra). Initial growth rates are slightly faster in conditioned GM-2 than in MCDB 131M DS or MCDB 120 DS without conditioning. However, colony-forming efficiencies are equivalent, and all of these media yield large numbers of clonal cultures that can readily be grown up to confluent monolayers and stored frozen.

Because these studies were done with cloned human muscle satellite cells, they were focused exclusively on improvement of growth, with no immediate concern about expression of differentiated properties or overgrowth by fibroblasts. The net result has been the development of media that strongly favor growth of HMSC at the expense of differentiation. When grown in MCDB 120 or MCDB 131M with either SF or DS supplementation, the cultured cells tend to be highly elongated and quite fibroblastic in appearance. Careful examination of large colonies with Giemsa staining generally reveals a few multinucleate myotubes, and some additional fusion occurs when cultures are plated at higher densities and allowed to remain confluent with periodic refeeding.

The low level of differentiation in the new growth media makes it necessary to ask whether the cells may have lost their ability to fuse and express muscle-specific proteins. Evidence that this is not the case has been obtained by growing cultures to confluency in the growth media and then transferring them to a medium that favors differentiation, such as DME supplemented with 10 μg/ml insulin (DMEI), which was used by Pinset and Whalen (1985) supra, for similar studies on rat L6 cells.

Within 3 days after transfer to DMEI, the HMSC cells undergo extensive fusion to form multinucleate myotubes. This is accompanied by a major increase in creatine kinase specific activity. Preliminary electrophoretic studies indicate that most of the increase is due to enhanced levels of the MM and MB isozymes of creatine kinase. Spontaneous twitching has also been observed in HMSC cultures allowed to remain in DMEI for six days after transfer from DS growth media. Control cultures that are transferred into fresh DS or SF media show very little fusion or increase in creatine kinase specific activity.

The ability of media to support differentiation was examined by replacing the growth medium in confluent cultures with appropriate test media. Assays of this type have shown that insulin in excess of that carried over from the growth medium is not strictly needed for differentiation of HMSC, although the level of creatine kinase obtained in unsupplemented DME remains somewhat less than in DME plus insulin. The extent of differentiation in DME plus 2% horse serum, which has been used as a differentiationpromoting medium by many previous investigators, is also less than that in DMEI.

MCDB 131M and MCDB 120 are only slightly less supportive of differentiation than DME. Cultures transferred into these media plus insulin exhibit substantial fusion and creatine kinase synthesis, but not as extensive as in DMEI. Intermediate levels of differentiation are also observed in F10 or F12 plus insulin. Collagen coating of the dishes somewhat increases the level of creatine kinase synthesis in most media, but is not essential for differentiation of HMSC.

Differentiation is inhibited by SF both alone and in combination with 5% dFBS, both in DME and in the MCDB media. The specific combinations of components that are responsible for the inhibition have not yet been identified. Initial experiments suggest that complex interactions may be involved. In addition, FGF, which is not present in serum-free supplement SF, may be of lesser importance in control of differentiation of HMSC than in the mouse MM-14 myoblast cell line (Linkhart, T. A. et al. (1981) supra).

These studies strongly suggest that a sequential two medium approach to growth and differentiation of HMSC will be required. The present studies, which were done with clonal cultures and allowed optimization of the medium for growth without concern about differentiation or overgrowth by other cell types, have verified that conditions that are optimal for growth of HMSC do not favor their differentiation. In addition, the limited studies that have been completed on conditions that favor differentiation make it appear unlikely that culture conditions will be found that promote high levels of both growth and differentiation, which is to be expected, since extensive fusion removes large numbers of mononucleate cells from the proliferating pool.

The media described herein provide many advantages over existing serum-free and low-serum culture media for HMSC. The availability of optimized nutrient media that have been developed specifically for growth of HMSC will greatly facilitate use of these cells as model systems for the study of diverse aspects of normal and abnormal muscle development and function. The ability to grow HMSC in serum free medium provides purer HMSC progeny preparations suitable for transplantation. In addition, the ability to grow HMSC in a semi-defined medium, followed by differentiation in a highly defined medium, will open the way for many lines of research that could not readily be pursued in media containing large amounts of whole serum and other undefined additives.

The following examples are included for illustrative purposes only and are not intended to limit the scope of the invention.

All references cited herein are incorporated herein by reference in their entirety.

EXAMPLES

Example 1

MCDB 120 (Table 1) is a basal nutrient medium developed for the optimized clonal growth of HMSC. The starting point for optimization of the new medium was MCDB 131 (Knedler, A. and Ham, R. G. (1987)supra).

Dulbecco's modified Eagle medium (DME), medium F10, and other standard media were purchased as dry powders from GIBCO. MCDB media were prepared from the constituent chemicals in the inventors' laboratory. MCDB 13 1M was prepared according to the protocol for MCDB 131 (Knedler, A. and Ham, R. G. (1987) supra), except that the concentration of magnesium sulfate was reduced to 1.0 mM.

All biochemicals were from Sigma (St. Louis, Mo.) and all inorganic salts were from Fisher Scientific (Pittsburgh, Pa.), except as indicated. Epidermal growth factor (EGF) was from Collaborative Research (Waltham, Mass.). Fibroblast growth factor (FGF) was from BRL (Gaithersburg, Md.). Highly purified full length acidic FGF (prostatropin) was generously provided by Dr. Wallace McKeehan (W. Alton Jones Cell Science Center, Lake Placid, N.Y.). Water for medium preparation was prepared by reverse osmosis, followed by passage through a Milli-Q ion exchange system (Millipore, Bedford, Mass.).

The defined Supplements were obtained from the following sources: Bovine insulin, Sigma 1-5500; mouse EGF, Collaborative 40001; dexamethasone, Sigma D-1756; bovine serum albumin, Sigma A-7888; bovine fetuin (Pedersen), Sigma-F-2379. Fetuin prepared by the method of Spiro, R. G. (1960) J. Biol. Chem. 235:2860–2869) was from GIBCO (Santa Clara, Calif.).

Fetal bovine serum (FBS) and horse serum were obtained from Hazleton Research Products (Lenexa, Kans.). Human serum was from Irvine Scientific (Santa Ana, Calif.). Dialyzed sera were prepared as follows: A buffer consisting of 2.0 M Tris, 0.6 M citrate, and 0.4 M borate at pH 7.0 was diluted 1:40 into the serum (usually 25 ml of buffer added to 975 ml of serum) and the mixture was stirred for 30 min. on ice. The buffered serum was then transferred to tightly clamped dialysis bags and dialyzed at 4° C. against 100 volumes of deionized water for 3 days, with daily changes of water. This was followed by lyophilization and storage of the dialyzed solids at −20° C. Convenient amounts were periodically dissolved in saline solution A at 50 mg/ml (total weighed solids), adjusted to pH 7.6, sterilized by membrane filtration (0.2 μ, detergent-free), and stored frozen at −20° C. in small aliquots until needed.

Saline solution A (Shipley, G. D. and Ham, R. G. (1981) In Vitro 17:656–670) has the following composition: glucose, 10 mM; KCl, 3.0 mM; NaCl, 130 mM; $Na_2HPO_4 \cdot 7H_2O$, 1.0 mM; phenol red, 0.0033 mM;

Hepes, 30 mM; and NaOH as needed to adjust final pH to 7.6.

Chicken embryo extract was purchased from GIBCO. Bovine pituitary extract (BPE) was prepared in the inventors' laboratory as described (Ham, R. G. et al. (1987) supra; Hammond, S. L. et al. (1984) supra). Full strength BPE contains approximately 14 mg/ml protein (determined by the Lowry method with serum albumin as a standard). Dialyzed BPE (dBPE) was prepared by dialysis against deionized water for 3 days (100 volumes, with daily changes), followed by centrifugation at 27,000×g for 15 min., and sterilization by membrane filtration (0.2 μ detergent-free).

Early studies were done in media GM-1 (F10 supplemented with 15% FBS and 0.5% chicken embryo extract) as described by Blau and Webster (1981) supra. Most of the nutrient growth response titrations were done in medium MCDB 131M supplemented with 5.0% dialyzed fetal bovine serum (dFBS) and 0.5% dialyzed BPE (dBPE). During the course of the research described, a serum-free supplement designated SF was developed. In some cases, 30 ng/ml FGF was added to SF, as indicated in the text. These supplements were used for serum-free growth both with MCDB 131M and with MCDB 120. The complete serum-free media are described herein by the name of the nutrient medium followed by "SF" (or "SF+FGF" when FGF was also added). Doubly-supplemented media containing both SF and 5.0% dFBS are identified by the name of the nutrient medium followed by DS (or DS+FGF when FGF was also added).

Example 2

All cell growth experiments were done with clonal cultures of HMSC prepared by direct cloning of satellite cells isolated from tissue samples (Blau, H. M. and Webster, C. (1981) supra). Initial experiments were done with clonal cultures provided by Dr. Blau at Stanford University. Recent experiments have been done employing clonal cultures established from muscle biopsy discard tissue provided by Dr. Hans Neville, University of Colorado Health Sciences Center, Denver. In all cases, primary clonal cultures were grown up until there were enough cells for freezing (about 20 population doublings), and then stored frozen, as described by Blau and Webster (1981) supra.

Ampules containing about one million frozen cells were thawed and distributed to two 25 cm² flasks containing either medium GM-2, or, in more recent experiments, MCDB 131M DS or MCDB 120 DS. The cultures were grown with medium changes as needed until they were semi-confluent, at which time individual flasks were used to prepare the inoculum for clonal growth experiments or subcultured and again grown to semi-confluency.

Before the cellular inoculum was prepared, the test media were prepared and 5 ml amounts were placed in triplicate 60 mm tissue culture petri dishes (Lux, Miles Laboratory, Naperville, Ill.). The dishes containing the media were then equilibrated in the cell culture incubator (37° C., 5% $CO_2$ in air saturated humidity) for at least one hour.

To prepare the inoculum, the medium was removed from the culture flask and the cells were rinsed with 2.0 ml of 0.05% (w/v) trypsin plus 0.02% (w/v) EDTA in saline solution A (pH 7.6) and then incubated in 2.0 ml of the same solution at room temperature until they were rounded up and beginning to release from the culture surface. The flask was then rapped sharply against the bench top to release the remaining cells and 2.0 ml of the medium into which they were to be inoculated was added. The suspension was centrifuged gently (1000×g for 3 min) and the supernatant was discarded.

The cells were then resuspended in complete growth medium (or growth medium minus the component being tested). A sample was counted in a hemocytometer, and dilutions were made as needed to obtain the desired number of cells in an inoculum of 50 μl. For the experiments described herein, the number of cells inoculated has varied from 1000 to 100 cells per dish, with a downward trend as growth has been improved. Most current growth-response experiments are done with 200 cells per petri dish, and an inoculum of 100 cells per dish is used for determination of colony forming efficiencies.

Immediately after the inoculum was added, the dishes were swirled gently to ensure uniform distribution of the cells over the culture surface. The dishes were then incubated for 14 days without medium change. At the end of this period, the medium was discarded and the cells were fixed with methanol for 10 min. The dishes were then rinsed briefly with tap water. Two dishes from each set were then stained for 15 min. with 0.1% crystal violet in water for evaluation of growth, and the third was stained for 15 min. with Giemsa stain for evaluation of fusion.

Example 3

Total colony area per dish was determined with an Artek 880 colony counter that has been modified to detect areas with greater than a preset minimum stain density. (Edge detection circuits do not work well for cultures of HMSC because of the irregular densities and fuzzy edges of the colonies). Colony-forming efficiency was determined by direct count of colonies, usually with an inoculum of 100 cells per dish to minimize overlap of colonies.

Qualitative visual estimates of myotube formation were obtained from the Giemsa stained plates that were included in all routine clonal growth assays. Quantitative data on extent of differentiation were obtained by spectrophotometric determination of creatine kinase specific activity in dense cultures. For the 10 creatine kinase assays, a cell suspension was prepared with trypsin-EDTA as described above, counted, and diluted to 12,500–24,000 cells per ml in DS or SF media as indicated. Replicate 35 mm tissue culture petri dishes were inoculated with 2.0 ml aliquots of the cell suspension and the cultures were then grown to heavy confluency (typically 11 days without medium change).

The medium was then changed either to DME +10 μg/ml insulin (DMEI) to verify that the cultures had retained the ability to differentiate (Pinset, C. and Whalen, (1985) supra) or else to a medium that was being tested for its effects on differentiation. From 3 to 7 days after the medium change, the unfixed cells were rinsed twice with solution A, overlaid with 0.25 ml of 0.05M glycylglycine buffer at pH 6.75, frozen at −70° C., thawed, scraped from the culture surface, and vortexed, still in the glycylglycine buffer. Commercial kits were used to determine total creatine kinase activity (Sigma) and total protein (Biorad, Richmond, Calif.), and creatine kinase specific activity was calculated from the two values. In addition, creatine kinase isozyme distributions of selected cell lysates were examined with a commercial kit (Tital Gel-PC CPK-isozyme kit, Helena Laboratories, Beaumont, Tex.) to verify the relationship between increased specific activity and the presence of MB and MM isozymes.

Example 4

Crude fetuin prepared from fetal bovine serum (FBS) by precipitation with 45% saturated ammonium sulfate as described by Pedersen K. O. (1947) J Phys Colloid Chem. 51:164–171, has long been used to promote attachment and growth without serum of a variety of types of cultured cells (Fisher, H. W., Puck, T. T., and Sato, G. (1958) Proc. Natl. Acad. Sci. USA 44:4–10; Ham, R. G. (1963) Exp. Cell Res. 29:515–526; Puck, T. T., Waldren, C. A. and Jones, C. (1986) Proc. Natl. Acad. Sci. USA 59:192–199; Salomon, D. S., Liotta, L. A. and Kidwell, W. R. (1981) Proc. Natl. Acad. Sci. USA 78:362–382; Ham, R. G., St. Clair, J. A., Webster, C. and Blau, H. M. (1988) In Vitro Cell. Dev. Biol. 24:833–844, and many others). However, it has been controversial as to whether the biological activity resides in fetuin per se or in minor contaminants. Soon after the first demonstration of fetuin activity, Fisher, H. W., Puck, T. T., and Sato, G. (1958) Proc. Natl. Acad. Sci. USA 44:4–10, Lieherman I., Lamy, F. and Ove, P. (1959) Science 129:43–44, reported that fetuin purified by DEAE-cellulose chromatography was inactive and that the activity was in a separate fraction. Highly purified fetuin prepared as described by Spiro, R. G. (1960) J. Biol. Chem. 235:2860–2869 is biologically inactive in most growth assays (Puck, T. T., Waldren, C. A. and Jone, C. (1986) Proc. Natl. Acad. Sci. USA 59:192–199; Salomon, D. S., Liotta, L. A. and Kidwell, W. R. (1981) Proc. Natl. Acad. Sci. USA 78:362–382; Ham, R. G., St. Clair, J. A., Webster, C. and Blau, H. M. ( 1988 ) In Vitro Cell. Dev. Biol. 24:833–844; Fisher, H. W., O'Brien, D. and Puck, T. T. (1962) Arch. Biochem. Biophys. 99:241–248; Mart, A. G. M., Owen, J. A. and Wilson, G. S. (1962) Biochem. Biophys Acta 63.:276–285), and there have been numerous reports and extensive speculation that the biological activity of the crude fetuin preparations is carried by trace contaminants, rather than the fetuin itself (Salomon, D. S., Liotta, L. A. and Kidwell, W. R. (1981) Proc. Natl. Acad. Sci. USA 78:362–382; Fisher, H. W., O'Brien, D. and Puck, T. T. (1962) Arch. Biochem. Biophys. 99:241–248; Mart, A. G. M., Owen, J. A. and Wilson, G. S. (1962) Biochim. Biophys. Acta 63:276–285; Feldman, S. R., Gonias, S. L., Ney, K. A., Pratt, C. W. and Pizzo, S. V. (1984) J. Biol. Chem. 259:4458–4462; Libby, P, Raines, E. W., Cullinane, P. M. and Ross, R. (1985) J. Cell. Physiol. 125:357–366). However, the possibility of subtle denaturation or introduction of toxicity during the Spiro process, which used organic solvents and heavy metal ions, has been difficult to rule out (Spiro, R. G. (1960) J. Biol. Chem. 235:2860–2869; Florini, J. R. and Roberts, S. B. (1979) In Vitro 15:983–992; Florini, J. R. (1987) Muscle & Nerve 10:577–598; Green, W. A. and Kay, C. M. (1963) J. Biol. Chem. 238:3640–3644). Florini and Roberts (1979) In Vitro 15:983–992, reported that the ability of Spiro fetuin to support growth of the rat L6 myogenic cell line could be restored by removal of toxic levels of zinc and barium. In addition, Florini stated in a recent review (Florini, J. R. (1987) Muscle & Nerve 10:577–598) that use of various chromatographic methods, including reversed-phase HPLC, had failed to separate any active contaminant from the bulk fetuin protein. This suggested that the mitogenic activity for muscle cell might reside in fetuin itself.

The large amount of Pedersen fetuin needed (0.5 mg/ml) in the subject SF supplement to replace serum suggests that the actual activity is probably a minor contaminant originating from FBS. Because of the conflicting claims and the problems others have experienced in attempts to fractionate Pedersen fetuin, direct fractionation of FBS was undertaken to verify that its fetuinreplacing mitogenic activity for HMSC could be separated from fetuin. A fractionation procedure (McKeehah, W. L., Genereux, D. P. and Ham, R. G. (1978) Biochem. Biophys. Res. Comm. 80:1013–1021) that exploits the solubility of fetuin in polyethylene glycol solutions to separate it from other serum proteins (Loskutoff, D. J. (1978) J. Cell. Physiol. 96:361–370) was used. This method proved to be effective, and after separation from fetuin, the mitogenic activity for HMSC was further concentrated by FPLC anion exchange chromatography.

Except where noted, all biochemicals use in preparation of media, including Pedersen fetuin, were from Sigma (St. Louis, Mo.), and all inorganic salts were from Fisher Scientific (Pittsburgh, Mass.). FBS was from Irvine Scientific (Santa Ana, CA). DEAE-Cellulose was from Whatman BioSystems (Maidstone, England). Polyethylene glycol (PEG) (M. W. 6,000 ) and high molecular weight markers were from Sigma.

HMSC were prepared by direct cloning of satellite cells isolated from muscle tissue samples as described herein and in Ham, R. G., St. Clair, J. A. and Meyer, S. (1990) Adv. Exp. Med. Biol. 280:193–199). The primary clonal cultures used in the experiments described in this paper were derived from psoas muscle of a premature infant who died 26 days after birth (Cooperative Human Tissue Network).

Growth-promoting activity was determined by clonal growth of HMSC (Ham, R. G., et al. (1988) In Vitro Cell. Dev. Biol. 24:833–844) in a background medium of MCDB 120 SF minus fetuin. All media were prepared freshly from frozen stocks on the day of the experiment. Triplicate 60-mm tissue culture petri dishes, each containing 5 ml of test medium, were equilibrated in the cell culture incubator (37° C., 5% $CO_2$ in air, and saturated humidity) for at least an hour before inoculation with 300 to 500 HMSC in 50 $\mu$l of control medium. After 14 days of incubation without medium change, the cells were fixed and stained. Total colony area per dish was determined with an Artek 880 colony counter modified to detect areas with greater than a preset minimum stain density.

FBS was fractionated by sequential precipitation with ammonium sulfate and polyethylene glycol (PEG) as described previously (McKeeban, W. L., Genereux, D. P. and Ham, R. G. (1978) Biochem. Biophys. Res. Comm. 80:1013–1021). All the operations were carried out at 4° C. In summary, one liter FBS was precipitated with buffered 50% saturated ammonium sulfate. The precipitate was designated 50 AS and the supernatant 50 AS SN. 50 AS was redissolved and precipitated with 25% PEG, which precipitates virtually all proteins except fetuin (Loskutoff, D. J. (1978) J. Cell. Physiol. 96:361–370). The 25% PEG precipitate was redissolved, and loaded onto a DEAE-cellulose column, washed to remove the PEG, and eluted with 1.0 M NaCl (0.05 M Tris-HCl, pH 7.0). All fractions showing absorption at 280 nm were pooled together, and precipitated again with buffered 50% saturated ammonium sulfate. The precipitate was designated 50 PEG 2X. All three fractions: 50 AS, 50 AS SN, and 50 PEG 2X were dialyzed against Milli Q ™ water, lyophilized, and stored frozen at −20° C.

The fraction containing fetuin-replacing activity (50 PEG 2X) was chromatographed on an anion-exchange column (Mono Q HR 5/5, Pharmacia-LKB) using an FPLC system (Pharmacia-LKB) at 4° C. The column was equilibrated with 50 mM Tris-HCl (pH 8.0), and then eluted with 0% to 70% of 1.0 M NaCl in the same buffer with a linear gradient. All fractions were tested for mitogenic activity.

To obtain size information of the active fractions, 50 PEG 2X was loaded on a Sephadex G-150 (Pharmacia-LKB) column preequilibrated with phosphate buffer (pH 7.0) and precalibrated with molecular weight standards (Sigma). The column was eluted isocratically with the same buffer until well after the absorbance returned to the base line. All fractions were tested for mitogenic activity.

Analytical SDS-PAGE was carried out according to the method of Laemmli (21) in 7.5% polyacrylamide gel using a vertical slab gel apparatus (Protein II Slab Cell, BioRad). Fractions from FPLC anion-exchange chromatography were desalted and concentrated by ultrafiltration using Centricoh-3 membrane (Amicon) before applied to the gel.

Fractions 50 AS, 50 AS SN, and 50 PEG 2X were tested for their ability to support clonal growth of HMSC in MCDB 120 SF without fetuin. The most potent growth-promoting activity was in fraction 50 PEG 2X (FIG. 4), which contains very little fetuin. The activity of 50 PEG 2X was greater than that of the Pedersen fetuin control (120 SF) and brought the growth level close to that in MCDB 120 supplemented with both SF and 15% FBS.

50 PEG 2X was tested for both heat and pH stabilities. The activity was partially lost when heated at 60° C. for 30 rain and was totally destroyed by short term (3 min) boiling (Table 2). Overnight acidic (pH 2) or basic (pH 12) treatment (approximately 10 h) also substantially decreased mitogenic activity.

TABLE 2

Characterization of fetuin-replacing fraction 50 PEG 2

| Treatment | Experimental Total | Control Colony area (mm$^2$/dish) | 120SF-Fetuin |
|---|---|---|---|
| Heating | | 1318 | 0 |
| 60° C., 10 min | 1293 | | |
| 60° C., 30 min | 1095 | | |
| 100° C., 3 min | 0 | | |
| 100° C., 10 min | 0 | | |
| pH Treatment | | 1701 (at pH7) | 19 |
| pH 2, overnight | 246 | | |
| pH 12, overnight | 83 | | |
| Size (gel filtration) range | | 807 (+fetuin) | 8 |
| >150 kDa | 699 | | |
| 150–70 kDa | 417 | | |
| <70 kDa | 0 | | |

Clonal growth assays were performed with HMSC in MCDB120 SF minus, fetuin, and the gel filtration was done with Sephadex G-150, as described herein. In each case, the control was prepared under identical conditions except for absence of the experimental treatment.

Figure 5:
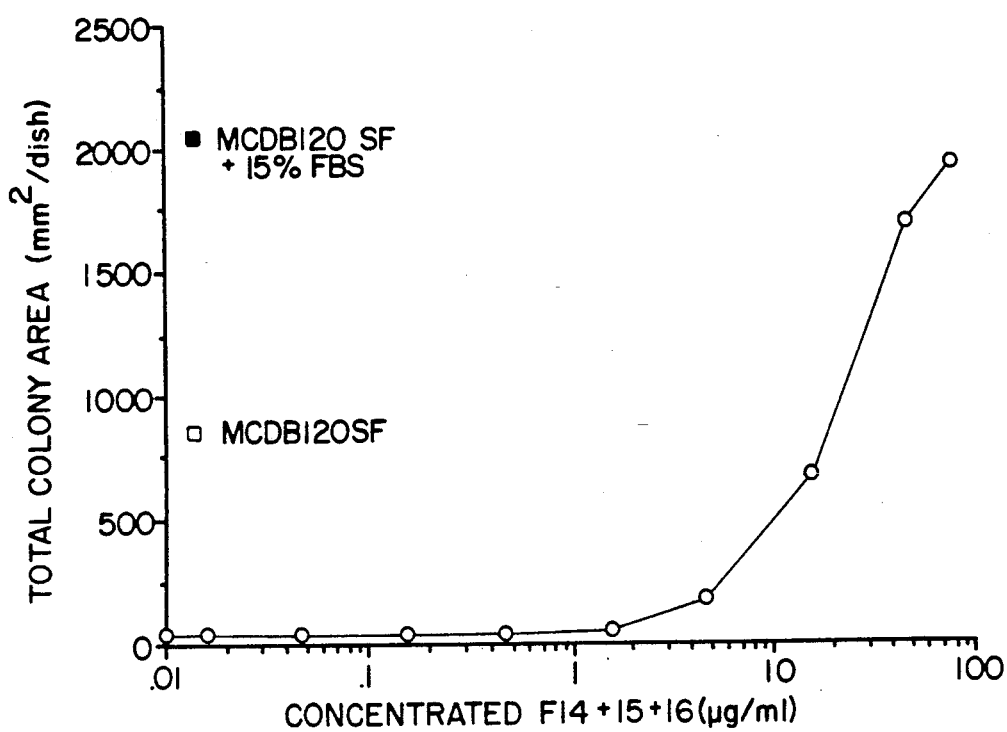
FIG. 5 illustrates a dose-response curve of combined FPLC fractions F14+15+16 for clonal growth of HMSC, as described in Example 4.

Since fetuin-replacing activity was contained in 50 PEG 2X, this fraction was subjected to further separation using FPLC anionexchange. The fetuin-replacing activity for HMSC started to rise from fraction 12, reached maximum at fraction 15, an then remained elevated until the absorbance returned to the base line. Most of the biological activity was eluted from the column in fractions 14, 15 and 16, just after the bulk of the protein. Fractions 14, 15 and 16 were pooled and used to obtain a dose-response curve for stimulation of growth of HMSC (FIG. 5). These three fractions were able to stimulate clonal growth well above the level obtained in MCDB 120 with complete SF, as had been the case with 50 PEG 2X. Due to limited amount of the fractions, the growth response curve could not be carried to saturation, but growth with the highest concentration tested approached that obtained the MCDB 120 SF plus 15% FBS.

All active fractions from Sephadex G-150 chromatography of 50 PEG 2X were above 70 kDa (Table 2). The most activity resided in two peaks of approximately 290 kDa and 130 kDa.

Figure 4:
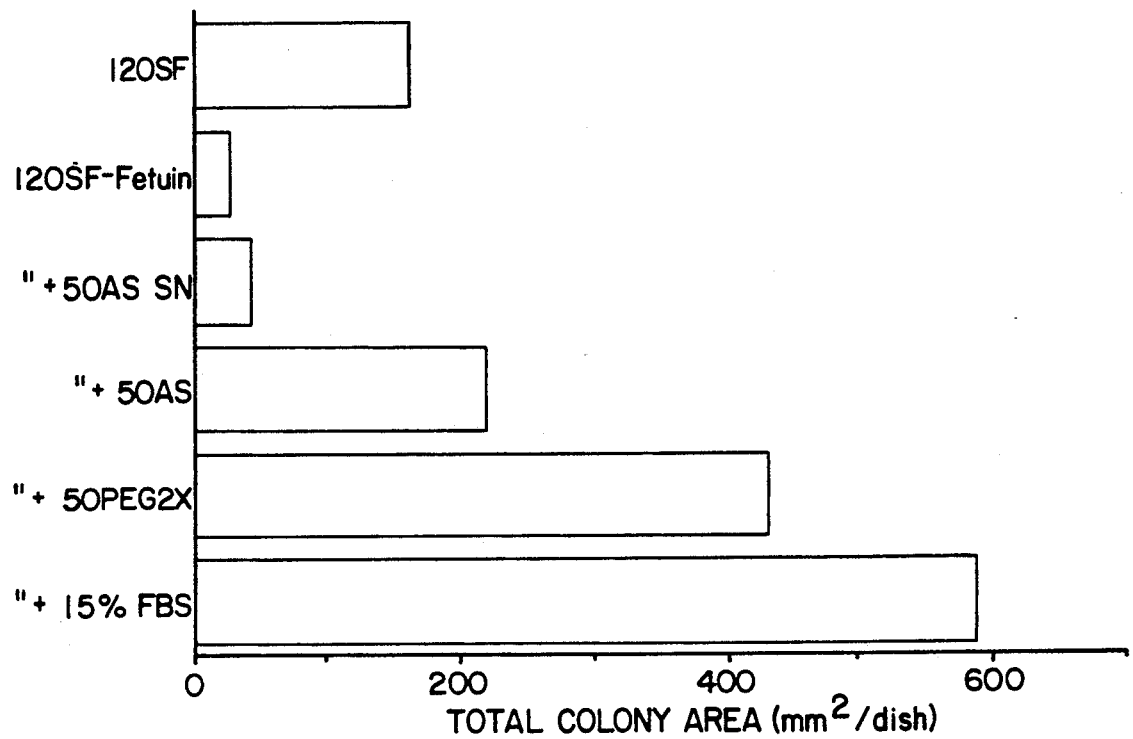
FIG. 4 depicts clonal growth responses of HMSC to MCDB 120 plus the indicated serum fractions. 500 μg/ml of each serum fraction was added to medium MCDB 120 SF minus fetuin. The mitogenic assay was performed as described in Example 4.

SDS-PAGE gels (FIG. 4 of Nie, Z. et al. (1991) Biochem. Biophys. Res. Com 178:959) indicated elimination of most of the fetuin and also the albumin from fraction 50 PEG 2X and from combined fractions 14, 15 and 16. Panel B of FIG. 4 of Nie, Z. et al. compares 50 PEG 2X and the combined fractions with better resolution. Several bands with molecular weight above about 80 kDa were intensified in combined fractions 14, 15 and 16 when compared to 50 PEG 2X, whereas bands in the expected weight range for fetuin and albumin were further reduced. This corresponds well with the size determination (Table 2) and indicates further that fetuin itself is not responsible for the growth. However, there were still a large number of proteins in the combined fractions, covering the whole range of resolution of the 7.5% polyacrylamide gel.

The specific activity and recovery of the partially purified fetuin-replacing fractions are presented in Table 3. The specific activity was determined at the half maximal response on a half-log step titration of the fractions. Relative to FBS, fraction 50 PEG 2X was purified about 11-fold for fetuin-replacing activity, with a 68% recovery. Combined fractions 14, 15 and 16 from the anionexchange column were purified 99-fold with an overall recovery of 30%.

TABLE 3

Specific activity of fractions and recovery

| Fraction | Specific activity (mm$^2$/mg) | Purification (fold) | Recovery (mg) | Total activity Recovery (mm$^2$) | Rate (%) |
|---|---|---|---|---|---|
| FBS | 88.7 | 1.0 | 37,260 | 3,304,962 | 100 |
| 50 AS | 126.2 | 1.4 | 16,865 | 2,128,363 | 64 |
| 50 PEG 2X | 1025.0 | 11.6 | 2,192 | 2,246,800 | 68 |
| F14 + 15 + 16 | 8788.9 | 99.1 | 111.8 | 982,599 | 30 |

The values shown were based on one liter of fetal bovine serum as the starting material. All the fractions were assayed with HMSC in MCDB 120 SF minus fetuin as described in Experimental Procedures. Specific activities were determined from the half maximum responded on a half-log step titration of the fractions. Activity units are based on the area of cell colonies as measured with the modified Artek counter.

The results presented herein have demonstrated that the mitogenic activity for HMSC is separable from fetuin and that fetuin itself is not required for serum-free growth of HMSC. The same also appears to be true for rat L6 cells (data not shown), except that, unlike HMSC, they fail to attach in the absence of fetuin or the fetuin-replacing activity. The potential relationship of this activity to many other substances reported to partially or completely replace the fetuin requirement for other cell types is discussed below.

1. Inhibition of trypsin: In most early cell culture, trypsin was usually not completely removed. Neutralization of trypsin appears to have been one of the major roles of crude fetuin in promoting serum-free growth under such condition. In experiments described herein, the cellular inoculum is washed and diluted with sufficient care to avoid this problem, and in many of the more critical experiments, tryptic action has been stopped with soybean trypsin inhibitor to rule out any possible residual effects.

2. DEAE fractions: Lieberman, I., Lamy, F. and Ove, P. (1959) Science 129:43–44 claimed to have separated an active contaminant fraction from inactive fetuin with DEAE-cellulose chromatography. However, because recovery was so low, critics suggested that they were denaturing most of the fetuin and leaving only a residual active fraction (Puck, T. T., Waldren, C. A. and Jone, C. (1968) Proc. Natl. Acad. Sci. USA 59:192–199; Fisher, H. W. O'Brien, D. and Puck, T. T. (1962) Arch. Biochem. Biophys. 99:241–248). Alternatively, the low activity may have reflected the need for both anti-tryptic activity and mitogenic activity. Nonetheless, there is little loss of activity either in the DEAE-binding and elution step in the preparation of 50 PEG 2X, or in the FPLC anion exchange purification (Table 3).

3. Polyamines: The fetuin requirement for serum-free clonal growth of Chinese hamster ovary cells (Ham, R. G. (1963) Exp. Cell Res. 29:515–526) was replaced by the addition of putrescine, spermidine, or spermine to the culture medium (Ham, R. G. (1964) Biophys. Biochem. Res. Commun. 14:34–38). The subject serum-free medium for HMSC contains a low level of putrescine, and additional amounts up to 10 $\mu$M have no effect on the requirement fetuin or the fetuin-replacing activity.

4. Fibronectin: Dollenmeier, P., Turner, D. C. and Eppenberger, H. M. (1981) Exp. Cell. Res. 135:47–61 suggested that fetuin might be a source of fibronectin for MM-1 cells. However, fibronectin does not replace fetuin in the 120-SF system (data not shown), or in others (Claycomb, W. C. (1980) Exp. Cell. Res. 131:231–236; Allen, R. E., Dodson, M. V., Luiten, L. S. and Boxhorn, L. K. (1985) In Vitro Cell. Dev. Biol. 21:636–640).

5. Alpha-2-macroglobulin: Early studies suggested that a portion of the growth-promoting activity of FBS was associated with the macroglobulin fraction (Mart, A. G .M., Owen, J. A. and Wilson, G. S. (1962) Biochim. Biophys. Acta 63:276–285). A high molecular weight fetuin contaminant growth factor initially called embryonin" (Salomon, D. S., Liotta, L. A. and Kidwell, W. R. (1981) Proc. Natl. Acad. Sci. USA 78:362–382; Salomon, D. S., Bano, M., Smith, K. B. and Kidwell, W. R. (1982) J. Biol. Chem. 257:14093–14101) has been shown to be alpha-2-macroglobulin (Feldman, S. R., Gonias, S. L., Ney, K. A., pratt, C. W. and pizzo, S. V. (1984) J. Biol. them. 259:4458–4462). Commercially prepared alpha-2-macroglobulin does not replace fetuin for HMSC (data not shown) or for rat muscle cells (Allen, R. E., Dodson, M. V., Luiten, L. S. and Boxhorn, L. K. (1985) In Vitro Cell. Der. Biol 21:636–640). However all of the fetuin-replacing activity is above 70 kDa and large proteins become more prominent as the activity is concentrated, suggesting that it might be a macroglobulin or a related protein.

6. Platelet derived growth factor (PDGF): Libby, P., Raines, E. W., Cullinane, P. M. and Ross, R. (1985) J. Cell. Physiol. 125:357–366 reported contaminant PDGF in fetuin and suggested that it might be responsible for mitogenic effects on smooth muscle cells. In addition, yablonka-Reuveni, Z., Balestreri, T. M. and Bowen-Pope, D. F. (1990) J. Cell Biol. 111:1623–1629 reported that PDGF-BB is mitogenic for mouse myoblasts. Both PDGF-AB and PDGF-BB have been tested and determined to be ineffective replacements for fetuin (data not shown).

7. FGF's: Serum is generally considered not to have appreciable levels of FGF-like activity, but Kardami, E., Spector, D. and Strohman, R. C. (1988) Dev. Biol. 126:19–28 were able to show that passage of horse serum over a heparin-Sepharose column eliminated its ability to support growth of primary avian myoblasts, and that the activity could be restored by the addition of FGF or a muscle-derived FGF-like factor. However, it has been found that neither acidic nor basic FGF can replace fetuin for growth of HMSC (data not shown).

8. Lipids: Pedersen fetuin contains associated lipoproteinlike particles that resemble high density lipoprotein (HDL) (Kumbla, L., Cayatte, A. J. and Subbiah, M. T. R. (1989) FASEB 3:2075 $\propto$ 2080). Possible implications for the subject invention have not yet been fully explored, but it must be noted that lipids are capable of stimulating serum-free growth of many types of cultured cells.

In summary, the present results have shown that the fetuinreplacing mitogenic activity of FBS for HMSC can be separated from fetuin. Thus, the biological activity of Pedersen fetuin appears to be due to the presence of other serum proteins that are not completely removed from this relatively crude serum fraction. A 99-fold enrichment of the mitogenic activity for HMSC with 30% recovery has been achieved. However, the most active fractions still contain numerous protein bands and additional purification will be needed for precise characterization of the active substance ( s ) in these fractions.

It will be apparent to those in the art that certain changes in the specific chemical components employed in the preparation of a growth medium can be tolerated without affecting the function or altering the effectiveness of the medium. Also, it will be appreciated that certain non-nutrient materials, e.g., antibiotics, can be added to a growth medium without affecting the functionality of the medium. It will also be understood that certain components of the nutrient medium or the serum-free supplements can be substituted for equivalent substances or for preparations from different sources or of different purity without affecting the functionality of the medium Any such substitutions and additions are contemplated to be encompassed herein. Since modification of the specific embodiments will be apparent to those of skill in the art, it is intended that this invention be limited only by the spirit and scope of the appended claims.

We claim:

1. Human muscle satellite cell growth medium MCDB 120.

2. The medium of claim 1 and an undefined supplement.

3. The medium of claim 2, wherein said undefined supplement comprises a component selected from the group consisting of fetal bovine serum, bovine pituitary extract, chicken embryo extract, and any combination thereof.

4. The medium of claim 1 and a serum-free supplement comprising dexamethasone, serum albumin, epidermal growth factor, and a mitogen preparation selected from the group consisting of fraction 50 PEG 2X comprising fetuinreplacing activity and combined FPLC anion exchange fractions F14+15+16 comprising fetuin-replacing activity purified from said fraction 50 PEG 2X.

5. The medium of claim 1 and a serum-free supplement selected from the group consisting of a first supplement comprising dexamethasone, serum albumin, epidermal growth factor, insulin and fraction 50 PEG 2X comprising fetuin-replacing activity and a second supplement comprising dexamethasone, serum albumin, epidermal growth factor, insulin, and combined FPLC anion exchange fractions F14+15+16 comprising fetuin-replacing activity purified from said fraction 50 PEG 2X.

6. A method of growing human muscle satellite cell progeny comprising growing a human muscle satellite cell in the growth medium of claim 1 and an undefined supplement.

7. The method of claim 6, wherein said undefined supplement comprises a component selected from the group consisting of fetal bovine serum, bovine pituitary extract, chicken embryo extract, and any combination thereof.

8. A method of growing human muscle satellite cell progeny comprising the step of growing a human muscle satellite cell in a culture comprising:
(a) a medium selected from the group consisting of MCDB 120 and MCDB 131M, and
(b) a serum-free supplement comprising dexamethasone, serum albumin, epidermal growth factor, and a mitogen preparation selected from the group consisting of fraction 50 PEG 2X comprising fetuin-replacing activity and combined FPLC anion exchange fractions F14+15+16 comprising fetuinreplacing activity purified from said fraction 50 PEG 2X.

9. The method of claim 8, wherein said serum free supplement comprises human serum albumin.

10. The method of claim 8, wherein said supplement comprises human epidermal growth factor.

11. The method of claim 8, wherein said supplement further comprises about $3 \times 10^{-5}$ M insulin.

12. The method of claim 8, wherein said culture further comprises fibroblast growth factor at a concentration between about 3 ng/ml and 30 ng/ml.

13. The method of claim 8, wherein said culture further comprises at least about 5% dialyzed fetal bovine serum.

14. The method of claim 8, wherein said progeny comprise at least about $10^6$ progeny cells.

15. A serum-free supplement comprising dexamethasone, serum albumin, epidermal growth factor and a mitogen preparation selected from the group consisting of fraction 50 PEG 2X comprising fetuin-replacing activity and combined FPLC anion exchange fractions F14+15+16 comprising fetuinreplacing activity purified from said fraction 50 PEG 2X.

* * * * *

UNITED STATES PATENT AND TRADEMARK OFFICE
CERTIFICATE OF CORRECTION

PATENT NO. : 5,324,656

DATED : June 28, 1994

INVENTOR(S) : Richard J. Ham, Judith A. St. Clair, Zetan Nie

It is certified that error appears in the above-indentified patent and that said Letters Patent is hereby corrected as shown below: At column 5, in Table 1, line 27, rewrite "Phenol Red (Na salt)$_2$" as --Phenol Red (Na salt)$^2$--. At column 6, line 31, please delete "the optimal concentration of arginine chosen for use in." At column 9, line 17, please rewrite "33s-s" as --33s-40s--. At column 9, line 22, please rewrite "eta!" as --et al--. At column 9, line 38, please rewrite "Lira" as --Lim--. At column 9, line 41, please rewrite "Lira" as --Lim--. At column 9, line 42, please rewrite "Der." as --Dev.--. At column 9, line 49, please rewrite "etal" as --et al--. At column 10, line 54, please rewrite "Askarias" as --Askanas--. At column 10, line 58, please rewrite "Der." as --Dev.--. At column 11, line 33, please rewrite "1991" as --1990--. At column 11, line 37, please rewrite "McKeehah" as --McKeehan--. At column 11, line 44, please rewrite " "SF-i" " as --"SF-1"--. At column 11, line 56, please rewrite "McKeehah" as --McKeehan--. At column 13, line 43, please rewrite "McKeehah" as --McKeehan--. At column 17, line 46, please rewrite "(198 1)" as --(1981)--. At column 18, line 5, please rewrite "rain" as --min--. At column 19, line 23, please rewrite "Lieherman" as --Lieberman--. At column 19, line 36, please rewrite "Mart" as --Marr--. At column 19, line 45, please rewrite "Mart" as --Marr--. At column 20, line 10, please rewrite "McKeehah" as --McKeehan--. At column 20, line 52, please rewrite "McKeeban" as --McKeehan--. At column 21, line 1, please rewrite "QTM" as --Q$^{TM}$--. At column 21, line 37, please rewrite "rain" as --min--. At column 23, line 42, please rewrite "Mart" as --Marr--. At column 23, line 51, please rewrite "pratt" as --Pratt-- and "pizzo" as --Pizzo--. At columns 23, line 52, please rewrite "them." as --Chem.--. At column 23, line 56, please rewrite "Der." as --Dev.--. At column 23, line 66, please rewrite "yablonka-Reuveni" as --Yablonka-Reuveni--. At column 24, line 17, please rewrite "3:2075a2080" as --3:2075-2080--.

Signed and Sealed this

Tenth Day of January, 1995

BRUCE LEHMAN

Attest:

*Attesting Officer*

*Commissioner of Patents and Trademarks*